United States Patent [19]

Mushabac

[11] 4,182,312
[45] Jan. 8, 1980

[54] DENTAL PROBE

[76] Inventor: David R. Mushabac, 919 Ocean Ave., Brooklyn, N.Y. 11226

[21] Appl. No.: 798,790

[22] Filed: May 20, 1977

[51] Int. Cl.$^2$ .............................................. A61B 5/10
[52] U.S. Cl. .................... 433/68; 128/776; 33/174 D; 264/16; 433/214
[58] Field of Search ............... 128/2 S, 2 V, 2.1 Z, 128/303.14, 303.17, 67, 134; 32/17, 40 R, DIG. 3, 26–27, 18–21, 71, 58, 67; 33/23 R, 23 M, 174 D, DIG. 5, 23 D; 264/16–19; 29/160.6

[56] References Cited

U.S. PATENT DOCUMENTS

| | | | |
|---|---|---|---|
| 3,359,982 | 12/1967 | Guiorguiev | 128/303.18 |
| 3,490,146 | 1/1970 | Guichet | 33/174 D |
| 3,664,731 | 5/1972 | Jex | 33/174 D |
| 3,777,740 | 12/1973 | Hokanson | 128/2.05 Z X |
| 3,812,858 | 5/1974 | Oringer | 128/303.14 |
| 3,916,529 | 11/1975 | Mousseau | 128/2.1 Z X |
| 3,943,913 | 3/1976 | Johnson | 128/2 S |
| 3,943,914 | 3/1976 | Grenfell et al. | 128/2 S |
| 4,112,587 | 10/1978 | Weiss et al. | 128/134 |

FOREIGN PATENT DOCUMENTS 75885   7/1961   France ...................... 128/2 S
157456  1/1962   U.S.S.R. .................... 128/2 S

OTHER PUBLICATIONS

Doolittle, A. M. et al., *An Electronic Patient–Contouring Device.*

*Primary Examiner*—Dalton L. Truluck
*Assistant Examiner*—Francis J. Jaworski
*Attorney, Agent, or Firm*—McAulay, Fields, Fisher & Goldstein

[57] ABSTRACT

A dental probe having a stylus which is connected through a rod to a three position transducer which produces three signals indicating the position of the probe at any point to which the probe is applied. The transducers are mounted on an index tray which is adapted to be fastened to the jaw of the patient. Thus the patient's jaw becomes the origin against which all measurements are made. A handle is connected to the probe in such a fashion that the dentist has three rotational degrees of freedom of movement without affecting the position of the end of the stylus. Contact between the tip of the stylus and the patient's tissue completes a circuit to turn on the recording mechanism which receives the transducers' outputs.

7 Claims, 6 Drawing Figures

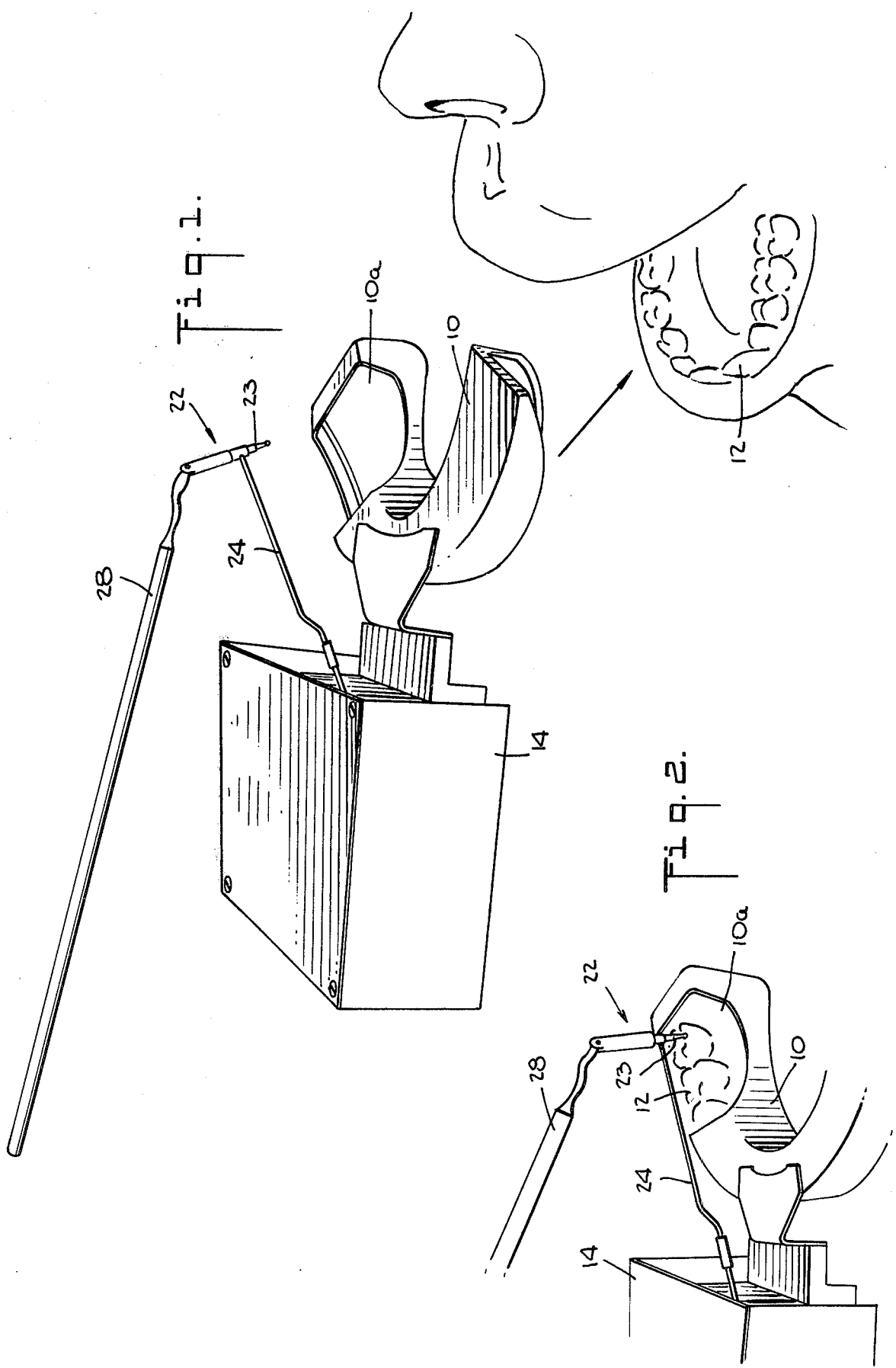

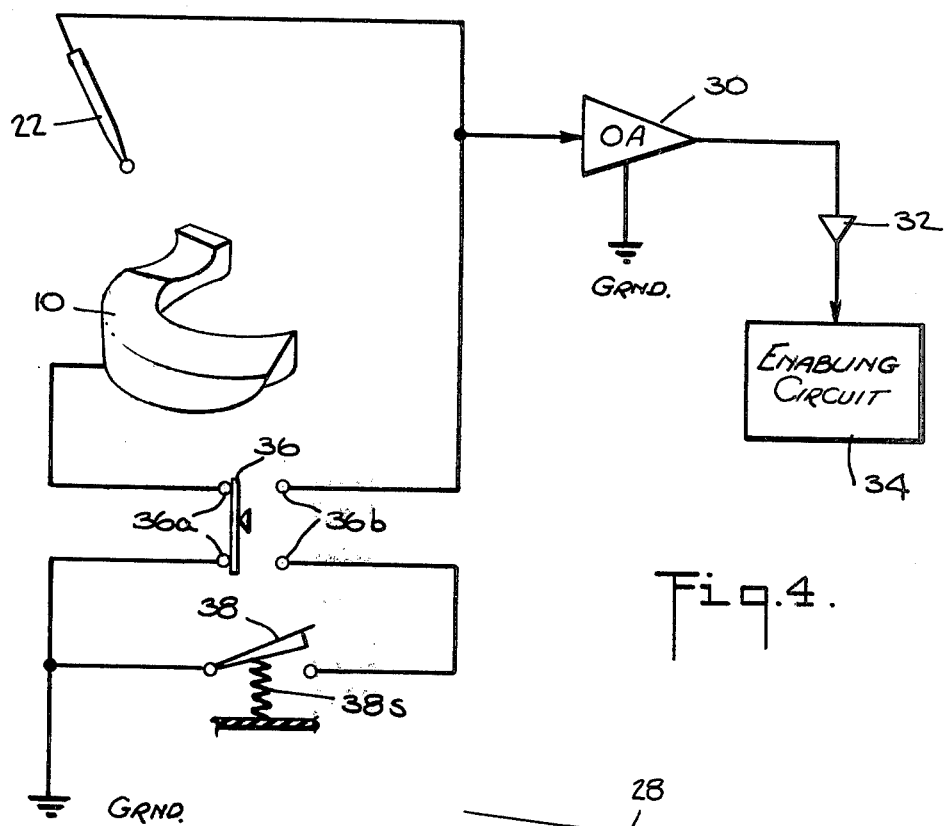
Fig. 4.
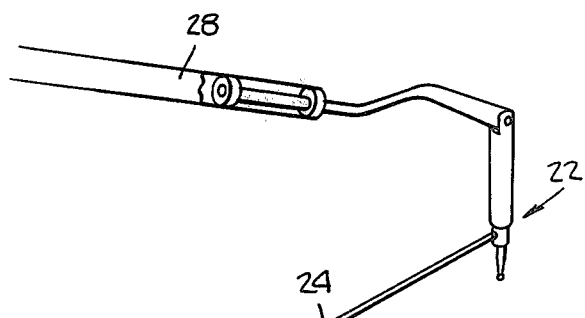
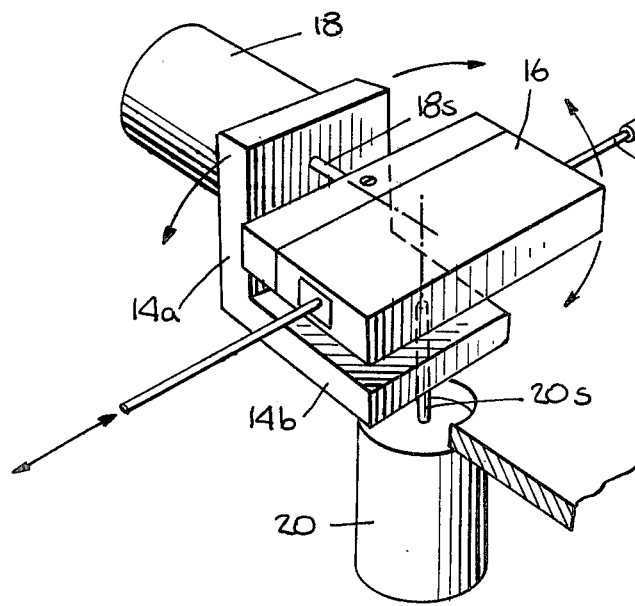
Fig. 3.

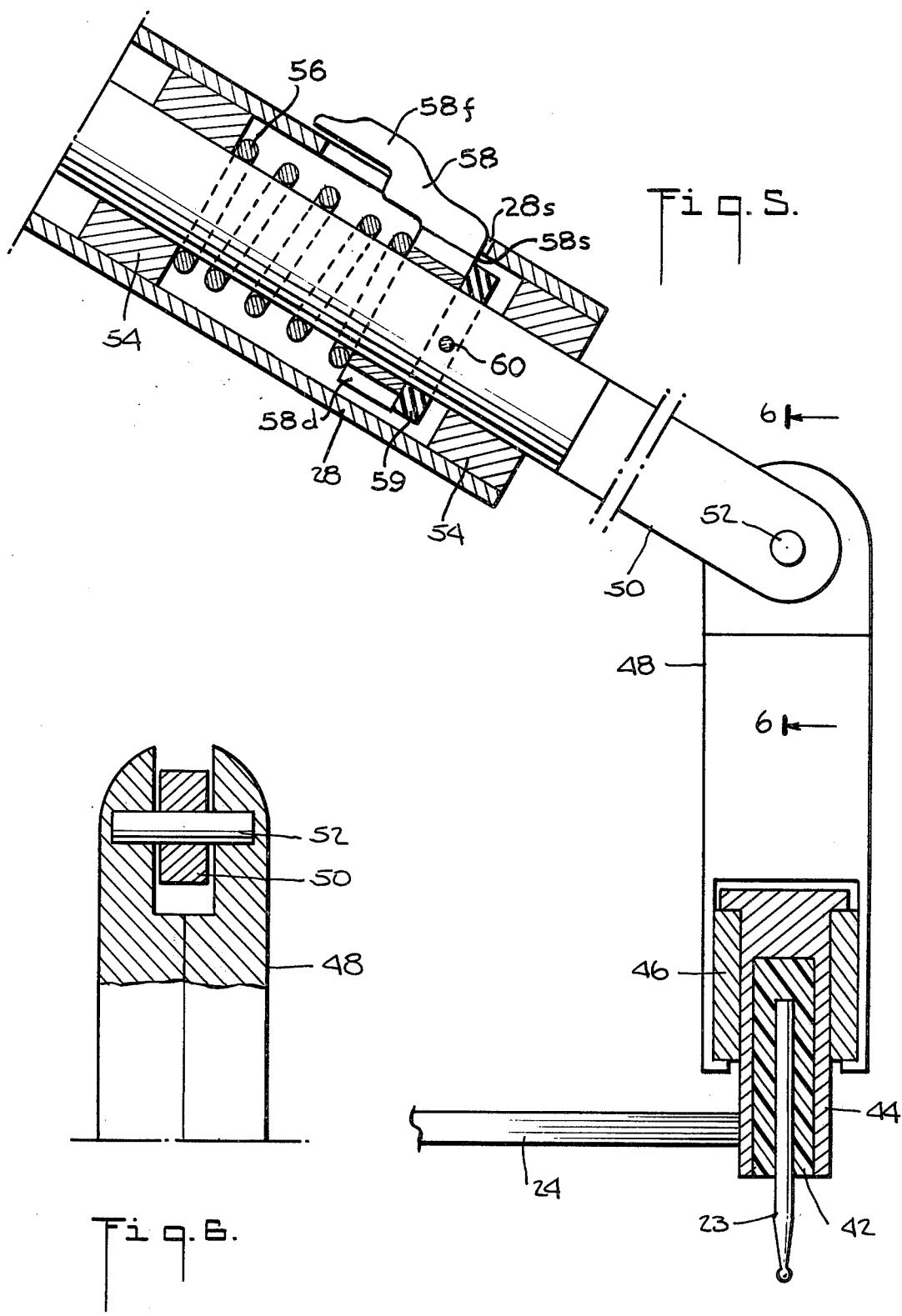

DENTAL PROBE

BACKGROUND OF THE INVENTION

This invention relates to a dental probe and more particularly to one that is adapted to provide the user with output electrical signals that provide three dimensional positional information.

In preparing a dental prosthesis, a complex and time consuming technique is generally employed in which impressions, measurements and molds are made with appreciable involvement by the dentist. Yet, modern electronic techniques have been available for a considerable period of time with which instruments, such as cutting instruments, can be automatically controlled to provide almost any structural form desired.

Accordingly, it is a major purpose of this invention to provide a link between the operation that must be performed by the dentist in providing a dental prosthesis and an automatically run tool for manufacturing the particular prosthesis.

In order for this link to be employed, it is important that it be relatively simple to use and be of a nature and structure with which the dentist is familiar. Accordingly, it is a further purpose of this invention to provide a dental probe or tracing apparatus similar in external configuration to what is now employed by dentists but which will provide an output signal that contains all the positional information needed to fully described the envelope of the required prosthesis.

It is a further purpose of this invention to provide such a probe or trace apparatus as can be used by the dentist in substantially the same fashion and by employing substantially the same manipulative techniques as are presently employed in the manipulation of a dental stylus.

Because of the medical nature of the apparatus involved, it is a further purpose of this invention that the device involved be safe to use and avoid imposing a substantial inconvenience on the patient.

BRIEF DESCRIPTION

In brief, this invention involves a probe, which may be of the usual dental type having a stylus, that is manipulated by the dentist by being applied to the teeth and gum tissues of a patient to provide a position indication of the points at which the probe is applied. This position indication is provided by virtue of the fact that a rod extending back from the probe and rigidly attached to the probe moves with the probe. This rod is connected to three position transducers. The three position transducers produce three signals which indicate the position of the probe at any point to which the probe is applied.

In one embodiment, the rod is attached to a minipotentiometer having an output that is linear with position along the potentiometer. This provides a measure of a first position parameter; in particular, the measure of the radius (R) parameter in polar coordinates. In that embodiment, the linear potentiometer is mechanically carried on two orthogonal rotary variable transformers each of which provides an amplitude output that is linear with angle thereby providing the theta ($\theta$) and phi ($\phi$) parameters of position in polar coordinates. The output of these three transducers provide a unique identification of the position of the tip of the probe.

It is normally desired to provide a position output only when the tip of the probe is in contact with the surface of the tooth or other mouth tissue so that the position information is surface position information only. To achieve this effect, a circuit is completed through the tooth and the gum when the metallic probe contacts the mouth tissue. It is only when this enabling current is completed that the transducer outputs are applied to whatever record is being kept.

An index tray is rigidly attached to the frame within which the transducers are mounted so as to provide a positional baseline or origin for the polar coordinates. This indexing tray is fastened to the jaw or head of the patient by means of a quick setting plaster. Thus the patient's jaw or head becomes the origin against which all measurements are made and movement of the patient's jaw does not affect the transducer outputs.

THE DRAWINGS

FIG. 1 is a perspective view of the device of this invention in position about to be placed over the lower teeth and lower jaw of the patient with a mount adapted to permit tracing a lower right area of teeth.

FIG. 2 illustrates the FIG. 1 device in position with the probe applied to one of the teeth of the patient.

FIG. 3 is a perspective view of the device of this invention with the outer housing of the transducer arrangement removed to show the relationship between the probe and the three transducers.

FIG. 4 is an electrical block and schematic diagram illustrating the relationship between an enabling circuit and a mode switch that permits this invention to be used in either of two modes.

FIG. 5 is a longitudinal cross-sectional view on an enlarged scale illustrating the relationships which provide three degrees of freedom of movement to the dentist without affecting the position of the stylus in the probe.

FIG. 6 is a cross-sectional view along the line 6—6 in FIG. 5.

DESCRIPTION OF THE PREFERRED EMBODIMENTS

The FIGS. all relate to the same embodiment of the invention. An aluminum indexing tray 10 has an inverted U-shaped configuration and is adapted to be placed over the teeth of the patient. When so placed, the tray 10 is fixed in place by the use of an appropriate dental plaster. An open area 10a provides access to teeth by the dentist when the tray is set in place on the patient's jaw. In the embodiment illustrated, the area 10a permits access to teeth and surrounding tissue in the lower right portion of the patient's jaw.

Rigidly connected to the tray 10 is a housing 14 in which are mounted three transducers 16, 18, 20. A dental probe 22, having a removable stylus 23, is connected to a linking rod 24 which moves with the probe 22. This rod 24 is connected to the positional input member 26 of a linear positional transducer 16. In brief, the heart of this transducer 16 is a minipotentiometer which provides an output electrical signal having a DC value that is a function of the position of the input member 26 and that is, preferably, a linear function of the position of the input member 26. Since the input member 26 is rigidly connected to the rod 24 which in turn is rigidly connected to the probe 22, the position of the probe 22 will command an output signal from the transducer 16 that can be considered to be the radial parameter in a polar coordinate system.

The shafts 18s and 20s of the two rotary variable transformers which provide the heart of the transducers 18 and 20 are mounted through openings in portions 14a and 14b of the frame 14. The shafts 18s and 20s are so mounted that they are free to rotate about their respective axes relative to the frame 14 and are also free to move in an axial direction relative to the frame 14. The radial parameter transducer 16 is mounted to the ends of each of the shafts 18s and 20s and is not otherwise supported on the frame 14. Thus rotation of the transducer 16 around the axis of either of these two shafts 18s and 20s will produce rotation of the corresponding transducer shaft 18s, 20s. As a consequence, the output of the transducer 18 is an electrical signal corresponding to the positional parameter theta ($\theta$) in a radial coordinate system and the output of the transducer 20 is a signal corresponding to the positional parameter phi ($\phi$) in a radial coordinate system. Both of the transducers 18 and 20 are preferably ones which provide a DC output signal having a value which is linear with the angle of the respective shaft 18s and 20s.

The transducer shafts 18s and 20s are positioned so that the axial lines of the two shafts are perpendicular to one another and also intersect. This relationship in addition to the fact that these transducer shafts are free to move axially relative to the frame 14 makes it possible for one or both of the shafts 18s, 20s, to rotate without binding the other shaft. The radius input shaft 26 must be orthogonal to the plane defined by the intersecting axial lines of the two rotational transformer shafts 18s and 20s.

The outputs of the three transducers 16, 18 and 20 are analog outputs which together provide a unique indication of position. They can be processed by any one of many known techniques to provide a continuous record of probe 22 position. As is known, they can be converted to digital signals, if desired, before being recorded. In any case, the arrangement of three transducers 16, 18, 20 to provide the result described above is a known arrangement and the detailed structures of the required transducers is known so that further disclosure of the details of the transducers is not deemed necessary here.

A handle 28 permits the dentist to properly manipulate the probe 22. The handle 28 is coupled to the probe 22 to support the probe 22 and to permit the dentist to move the probe 22 while making his trace yet permitting the dentist three degrees of freedom of movement without affecting the probe 22. The dentist thus has unrestrained wrist action to allow ready access to all parts of the tooth and surrounding tissue and to permit the dentist to position his hand while guiding the probe so that he will have optimum visibility.

FIG. 4 schematically illustrates the simple electrical arrangement that is employed in order to make sure that the probe 22 position is recorded only when contact is made between the probe 22 and the patient's tissues. An operational amplifier 30 has its output connected to an inverter 32 which in turn is connected to the input of an enabling circuit 34. When the input shown of the operational amplifier 30 is grounded then the input to the inverter 32 is at a zero level and the inverter provides an output that causes the enabling circuit 34 to enable or turn on all of the signal processing circuitry.

The input to the operational amplifier 30 can be grounded in either one of two modes as determined by the mode switch 36. When in the condition shown in FIG. 4, the mode switch 36 grounds the electrically conductive tray 10. The tray 10 can be made of aluminum. In that mode, whenever the dentist applies the probe 22 to the patient's tooth or gum tissues, an electrical circuit is completed from the probe 22, and thus from the input to the operational amplifier 30, through the conductive saline media of the patient's mouth to the tray 10 and thus to the ground. In this fashion the input to the operational amplifier 30 is grounded and the enabling circuit 34 has an input that causes it to enable or turn on the recording circuitry.

In a second mode, the mode switch 36 is thrown to open the contacts 36a and close the contacts 36b. In this mode, the input to the operational amplifier 30 bypasses the probe 22 and tray 10 and is applied to one side of a foot switch 38. The footswitch 38 is spring loaded by spring 38s to the open position shown in FIG. 4. But if the dentist closes the foot switch 38, it will ground the input of the operational amplifier, providing the switch 36 is thrown to the second mode, and thereby provide the required enabling signals to record whatever position the probe 22 is in while the foot switch 38 is depressed. In this fashion, the dentist can trace out and record a contour or position even without contacting the patient's tissues.

In brief, mode one requires probe 22 contact to patient tissue while mode two requires that a foot pedal be closed.

The handle 28 and probe 22 arrangement can best be understood from FIG. 5 and FIG. 6. As shown therein, the stylus 23 is fixedly held in a plastic chuck 42 which in turn is fixedly held in the probe shell 44. Because of this chuck arrangement which operates by virtue of a friction hold, this stylus 23 can be replaced. The linking rod 24 to the transducers is fixedly attached to the probe shell 44. The probe shell 44 is journaled in a bearing 46 within a housing 48. The bearing 46 can be of the type used in dental air turbine drills. Because of the bearing 46, the housing 48 can rotate about the axis of the stylus 23 without affecting the position of the stylus. An interconnecting rod 50 is rotatably mounted through a pin 52 to the housing 48 thereby permitting rotational movement of the interconnecting rod 50 relative to the housing 48 about the axis of the pin 52. The interconnecting rod 50 is journaled through bearings 54 within the handle 28. These bearings 54 are the same type as the bearings 46 and permit rotational movement of the handle 28 about the axis of the interconnecting rod 50.

The FIG. 5 arrangement illustrates that the dentist can have three degrees of freedom of movement without affecting the position of the stylus 23 thereby facilitating the positioning of his hand preparatory to moving the stylus 23. These three degrees of freedom of rotation are (1) the rotation of the handle 28 about its own axis because of the bearings 54 on which the handle 28 is journaled, (2) the rotation of the handle 28 about the axis of the pin 52 because of the mounting of the interconnecting rod 50 on the pin 52, and (3) rotation of the handle 28 around the axis of the stylus 23 because of the mounting of the housing 48 on the journal bearing 46.

It would be inconvenient for the handle 28 to freely rotate about its own axis and thus provision is made so that such rotation will occur only upon actuation of a spring 56 loaded frictional clamp mechanism 58, 59 illustrated in FIG. 5. The finger actuated lock mechanism 58 is consituted by finger portion 58f and an annular disc like portion 58d. The disc like portion 58d is mounted on the connecting rod 50 and has a slip fit relationship therewith so that the lock number 58 can be moved axially along the rod 50 and also so that the rod 50 can rotate within the central opening of the disc like portion 58d. The finger portion 58f extends outwardly through a slot 28s in the wall of the tubular handle 28. This slot 28s extends over a length sufficient so that the finger portion 58f can be retracted from the protracted position shown in FIG. 5. When in the protracted position shown in FIG. 5, the surface 58s of the lock number 58 frictionally engages an annular member 59 that is fixed to the rod 50 by pin 60. Because the body of the lock member 58 engages the walls of the slots 28s of the handle 28, the frictional engagement between the surface 58s and the adjacent surface of the annular member 59 prevents rotation of the handle 28 on the rod 50. However, when the dentist wishes to rotate the handle 28 relative to the rod 50, he pushes the finger portion 58f to the left, as shown in FIG. 5, and thereby retracts the lock number 58 against the force of the spring 56 disengaging lock number 58 and annular member 59. When so disengaged, the handle 29 is free to rotate relative to the rod 50 because there is only a slip fit relationship between the lock member 58 and the rod 50.

When the dentist does wish to affect the position of the probe 22 after he had adjusted the position of his hand so that it is convenient both in terms of wrist action and so that he can see the teeth and tissue which he plans to trace, he then pushes forward on the handle 28 in order to cause the probe 22 to move forward. He can also move the probe 22 right and left by holding his hand steady and moving it right and left. Furthermore, he can move his hand up and down, without rotating about the pin 30, so as to move the probe 22 up and down.

When the dentist has achieved a position that permits him to touch and see the portion of the tooth or tissue that he wishes to record, he can then touch that portion of the patient's mouth thereby grounding the enabling circuit that causes the position signals to be recorded. He then moves the probe 22 along the surface of the tooth and tissue involved by pushing forward on the handle 28, or moving his hand right or left by lifting up or pushing down. He will thereby provide a series of signals through the transducers 16, 18 and 20 that will represent the line being traced.

The signals provided by the device of this invention are a set of positional information signals that can later be used to control the position and movement of a drill thereby providing a prosthesis congruent to the shape traced by the probe 22. If the probe 22 and the drill used to make the prosthesis are in turn congruent to one another, then the programming of the drilling apparatus is greatly simplified and the retracing of the surface initially traced by the probe 22 under the control of the dentist will provide a prosthesis precisely as prescribed by the dentist during his manipulation with the probe 22. In order to permit the capability of having a series of probes 22 employed which are congruent to the drills ultimately used in making the prosthesis, it is necessary that the stylus 23 be replaceable as is shown in FIG. 5. The stylus 23 can be replaced by any one of a number of different styli as a function of the nature and shape of the drilling tool which will be employed to affect the manufacture of the prosthesis involved.

What is claimed is:

1. A dental trace apparatus for providing signals corresponding to the position of intra-oral tissues, including teeth, of a patient, comprising:
  a three dimensional position transducer to provide position signals,
  a dental probe operable to probe intra-oral tissues of a patient and operably coupled to said transducer to generate said signals, said signals indicating the position of said probe,
  enabling means responsive to contact between said probe and patient's intra-oral tissues to enable said transducer,
  said transducer providing said position signals only when enabled, and
  indexing means adapted to conform to and to be rigidly connected to the jaw of the patient to which jaw the intra-oral tissues are anchored as a part of the anatomy, and said transducer being achored to said indexing means thereby to form an origin point for said signals which is fixed with respect to the jaw of the patient, and may move with movement of the patient's jaw, head or body with no effect on the transducer signal generation.

2. The dental trace apparatus of claim 1 further comprising:
  switch means electrically parallel to said enabling means, said switch means when activated enabling said transducer to provide said position signals on a continuing basis regardless of contact between said probe and patient tissue.

3. The dental trace apparatus of claim 1 further comprising:
  a handle attached to said dental probe, said handle being capable of three degrees of rotational movement, whereby an operator may manipulate the handle without causing motion of said probe.

4. The dental trace apparatus of claim 3 further comprising:
  switch means electrically parallel to said enabling means, said switch means when activated enabling said transducer to provide said position signal on a continuing basis regardless of contact between said probe and patient tissue.

5. The dental trace apparatus of claim 3 wherein said handle comprises:
  a handle portion, a first extension portion and a second extension portion,
  said handle portion and said first extension portion having a sleeve and rod mounting relationship to one another to permit rotational movement of said handle about its axis relative to said first extension portion,
  said first extension portion and said second extension portion being pinned to one another to provide rotational movement of said first extension portion relative to said second extension portion about the axis of said pin,
  said second extension portion being mounted to said probe and comprising sleeve and rod positions to permit rotational movement of said sleeve of said second extension portion relative to the axis of said probe.

6. In a method of manufacturing dental prosthetic devices using an automatic program controlled cutting or milling instrument to conform the prosthetic device to a patient's intra-oral tissues, the steps comprising:
  probing the patient's intra-oral tissues including teeth with a dental trace apparatus claimed in claim 1 to provide a series of position signals related to the position of the intra-oral tissues; and
  recording said series of position signals.

7. The method of claim 6 further comprising the step of: selecting a series of probe styli for use that are congruent to the series of drills intended to be used in preparing the prosthetic device.

* * * * *